United States Patent
Cox et al.

(10) Patent No.: US 10,238,406 B2
(45) Date of Patent: Mar. 26, 2019

(54) METHODS AND APPARATUS FOR TREATING EMBOLISM

(71) Applicant: Inari Medical, Inc., Irvine, CA (US)

(72) Inventors: Brian J. Cox, Laguna Niguel, CA (US); Paul Lubock, Monarch Beach, CA (US); Robert Rosenbluth, Laguna Niguel, CA (US); Richard Quick, Mission Viejo, CA (US); Philippe Marchand, Lake Forest, CA (US)

(73) Assignee: Inari Medical, Inc., Aliso Viejo, CA (US)

( * ) Notice: Subject to any disclaimer, the term of this patent is extended or adjusted under 35 U.S.C. 154(b) by 214 days.

(21) Appl. No.: 15/031,102

(22) PCT Filed: Oct. 21, 2014

(86) PCT No.: PCT/US2014/061645
§ 371 (c)(1),
(2) Date: Apr. 21, 2016

(87) PCT Pub. No.: WO2015/061365
PCT Pub. Date: Apr. 30, 2015

(65) Prior Publication Data
US 2016/0287276 A1    Oct. 6, 2016

Related U.S. Application Data

(63) Continuation-in-part of application No. 14/299,933, filed on Jun. 9, 2014, now Pat. No. 9,259,237, and a
(Continued)

(51) Int. Cl.
*A61B 17/221* (2006.01)
*A61M 25/01* (2006.01)
*A61B 17/22* (2006.01)

(52) U.S. Cl.
CPC ........... *A61B 17/221* (2013.01); *A61M 25/01* (2013.01); *A61B 2017/22034* (2013.01); *A61B 2017/22067* (2013.01); *A61B 2017/22068* (2013.01)

(58) Field of Classification Search
CPC ........ A61B 17/221; A61B 2017/22034; A61B 2017/22067; A61B 2017/22068; A61M 25/01
See application file for complete search history.

(56) References Cited

U.S. PATENT DOCUMENTS 2,955,592 A    10/1960 MacLean
3,088,363 A    5/1963 Sparks
(Continued)

FOREIGN PATENT DOCUMENTS

JP    6190049    7/1994
JP    2001522631    5/1999
(Continued)

OTHER PUBLICATIONS

International Search Report and Written Opinion for International App. No. PCT/US2015/034987 filed Jun. 9, 2015, Applicant: Inceptus Medical, LLC, dated Sep. 17, 2015, 12 pages.
(Continued)

*Primary Examiner* — Tuan V Nguyen
(74) *Attorney, Agent, or Firm* — Perkins Coie LLP

(57) ABSTRACT

A device and method for intravascular treatment of an embolism, and particularly a pulmonary embolism, is disclosed herein. One aspect of the present technology, for example, is directed toward a clot treatment device that includes a support member having a plurality of first clot engagement members and second clot engagement members positioned about the circumference of a distal portion of the support member. In an undeployed state, individual first clot
(Continued)

engagement members can be linear and have a first length, and individual second clot engagement members can be linear and have a second length that is less than the first length. The clot engagement members can be configured to penetrate clot material along an arcuate path and hold clot material to the clot treatment device.

13 Claims, 10 Drawing Sheets

Related U.S. Application Data continuation-in-part of application No. 14/299,997, filed on Jun. 9, 2014, now abandoned.

(60) Provisional application No. 61/949,953, filed on Mar. 7, 2014, provisional application No. 61/893,859, filed on Oct. 21, 2013.

(56) References Cited

U.S. PATENT DOCUMENTS

| | | | |
|---|---|---|---|
| 3,435,826 A | 4/1969 | Fogarty | |
| 3,923,065 A | 12/1975 | Nozick et al. | |
| 4,030,503 A | 6/1977 | Clark, III | |
| 4,393,872 A | 7/1983 | Reznik et al. | |
| 4,650,466 A | 3/1987 | Luther | |
| 4,873,978 A | 10/1989 | Ginsburg | |
| 4,883,458 A | 11/1989 | Shiber | |
| 4,890,611 A | 1/1990 | Monfort et al. | |
| 5,011,488 A | 4/1991 | Ginsburg | |
| 5,059,178 A | 10/1991 | Ya | |
| 5,100,423 A | 3/1992 | Fearnot | |
| 5,102,415 A | 4/1992 | Guenther et al. | |
| 5,129,910 A | 7/1992 | Phan et al. | |
| 5,192,286 A | 3/1993 | Phan et al. | |
| 5,192,290 A | 3/1993 | Hilal | |
| 5,364,345 A | 11/1994 | Lowery et al. | |
| 5,370,653 A | 12/1994 | Cragg | |
| 5,443,443 A | 8/1995 | Shiber | |
| 5,476,450 A | 12/1995 | Ruggio | |
| 5,490,859 A | 2/1996 | Mische et al. | |
| 5,746,758 A | 5/1998 | Nordgren et al. | |
| 5,749,858 A | 5/1998 | Cramer | |
| 5,766,191 A | 6/1998 | Trerotola | |
| 5,827,304 A | 10/1998 | Hart | |
| 5,868,708 A | 2/1999 | Hart et al. | |
| 5,873,866 A | 2/1999 | Kondo et al. | |
| 5,873,882 A | 2/1999 | Straub et al. | |
| 5,876,414 A | 3/1999 | Straub | |
| 5,882,329 A | 3/1999 | Patterson et al. | |
| 5,941,869 A | 8/1999 | Patterson et al. | |
| 5,972,019 A | 10/1999 | Engelson et al. | |
| 5,974,938 A | 11/1999 | Lloyd | |
| 5,993,483 A | 11/1999 | Gianotti | |
| 6,066,149 A | 5/2000 | Samson et al. | |
| 6,066,158 A | 5/2000 | Engelson et al. | |
| 6,152,946 A | 11/2000 | Broome et al. | |
| 6,168,579 B1 | 1/2001 | Tsugita | |
| 6,203,561 B1 | 3/2001 | Ramee et al. | |
| 6,221,006 B1 | 4/2001 | Dubrul et al. | |
| 6,238,412 B1 | 5/2001 | Dubrul et al. | |
| 6,254,571 B1 | 7/2001 | Hart | |
| 6,258,115 B1 | 7/2001 | Dubrul | |
| 6,306,163 B1 | 10/2001 | Fitz | |
| 6,350,271 B1* | 2/2002 | Kurz | A61B 17/22031 606/127 |
| 6,364,895 B1 | 4/2002 | Greenhalgh | |
| 6,368,339 B1 | 4/2002 | Amplatz | |
| 6,383,205 B1 | 5/2002 | Samson et al. | |
| 6,413,235 B1 | 7/2002 | Parodi | |
| 6,423,032 B2 | 7/2002 | Parodi | |
| 6,440,148 B1 | 8/2002 | Shiber | |
| 6,454,741 B1 | 9/2002 | Muni et al. | |
| 6,454,775 B1 | 9/2002 | Demarais et al. | |
| 6,458,139 B1 | 10/2002 | Palmer et al. | |
| 6,511,492 B1 | 1/2003 | Rosenbluth et al. | |
| 6,514,273 B1 | 2/2003 | Voss et al. | |
| 6,530,935 B2 | 3/2003 | Wensel et al. | |
| 6,530,939 B1 | 3/2003 | Hopkins et al. | |
| 6,544,279 B1 | 4/2003 | Hopkins et al. | |
| 6,551,342 B1 | 4/2003 | Shen et al. | |
| 6,589,263 B1 | 7/2003 | Hopkins et al. | |
| 6,596,011 B2 | 7/2003 | Johnson et al. | |
| 6,602,271 B2 | 8/2003 | Adams et al. | |
| 6,605,074 B2 | 8/2003 | Zadno-Azizi et al. | |
| 6,605,102 B1 | 8/2003 | Mazzocchi et al. | |
| 6,635,070 B2 | 10/2003 | Leeflang et al. | |
| 6,645,222 B1 | 11/2003 | Parodi et al. | |
| 6,660,013 B2 | 12/2003 | Rabiner et al. | |
| 6,663,650 B2 | 12/2003 | Sepetka et al. | |
| 6,685,722 B1 | 2/2004 | Rosenbluth et al. | |
| 6,692,504 B2 | 2/2004 | Kurz et al. | |
| 6,699,260 B2 | 3/2004 | Dubrul et al. | |
| 6,755,847 B2 | 6/2004 | Eskuri | |
| 6,767,353 B1 | 7/2004 | Shiber | |
| 6,800,080 B1 | 10/2004 | Bates | |
| 6,939,361 B1 | 9/2005 | Kleshinski | |
| 6,960,222 B2 | 11/2005 | Vo et al. | |
| 7,004,954 B1 | 2/2006 | Voss et al. | |
| 7,036,707 B2 | 5/2006 | Aota et al. | |
| 7,041,084 B2 | 5/2006 | Fojtik | |
| 7,052,500 B2 | 5/2006 | Bashiri et al. | |
| 7,056,328 B2 | 6/2006 | Arnott | |
| 7,069,835 B2 | 7/2006 | Nishri et al. | |
| 7,179,273 B1 | 2/2007 | Palmer et al. | |
| 7,220,269 B1 | 5/2007 | Ansel et al. | |
| 7,232,432 B2 | 6/2007 | Fulton, III et al. | |
| 7,244,243 B2 | 7/2007 | Lary | |
| 7,285,126 B2 | 10/2007 | Sepetka et al. | |
| 7,306,618 B2 | 12/2007 | Demond et al. | |
| 7,320,698 B2 | 1/2008 | Eskuri | |
| 7,323,002 B2 | 1/2008 | Johnson et al. | |
| 7,331,980 B2 | 2/2008 | Dubrul et al. | |
| 7,534,234 B2 | 5/2009 | Fojtik | |
| 7,578,830 B2 | 8/2009 | Kusleika et al. | |
| 7,621,870 B2 | 11/2009 | Berrada et al. | |
| 7,674,247 B2 | 3/2010 | Fojtik | |
| 7,691,121 B2 | 4/2010 | Rosenbluth et al. | |
| 7,763,010 B2 | 7/2010 | Evans et al. | |
| 7,766,934 B2 | 8/2010 | Pal et al. | |
| 7,905,896 B2 | 3/2011 | Straub | |
| 7,938,820 B2 | 5/2011 | Webster et al. | |
| 7,976,511 B2 | 7/2011 | Fojtik | |
| 7,993,302 B2 | 8/2011 | Hebert et al. | |
| 7,993,363 B2 | 8/2011 | Demond et al. | |
| 8,043,313 B2 | 10/2011 | Krolik et al. | |
| 8,052,640 B2 | 11/2011 | Fiorella et al. | |
| 8,066,757 B2 | 11/2011 | Ferrera et al. | |
| 8,070,791 B2 | 12/2011 | Ferrera et al. | |
| 8,075,510 B2 | 12/2011 | Aklog et al. | |
| 8,088,140 B2 | 1/2012 | Ferrera et al. | |
| 8,100,935 B2 | 1/2012 | Rosenbluth et al. | |
| 8,109,962 B2 | 2/2012 | Pal | |
| 8,118,829 B2 | 2/2012 | Carrison et al. | |
| 8,197,493 B2 | 6/2012 | Ferrera et al. | |
| 8,246,641 B2 | 8/2012 | Osborne et al. | |
| 8,261,648 B1 | 9/2012 | Marchand et al. | |
| 8,298,257 B2 | 10/2012 | Sepetka et al. | |
| 8,317,748 B2 | 11/2012 | Fiorella et al. | |
| 8,337,450 B2 | 12/2012 | Fojtik | |
| RE43,902 E | 1/2013 | Hopkins et al. | |
| 8,357,178 B2 | 1/2013 | Grandfield et al. | |
| 8,361,104 B2 | 1/2013 | Jones et al. | |
| 8,409,215 B2 | 4/2013 | Sepetka et al. | |
| 8,486,105 B2 | 7/2013 | Demond et al. | |
| 8,491,539 B2 | 7/2013 | Fojtik | |
| 8,512,352 B2 | 8/2013 | Martin | |
| 8,535,334 B2 | 9/2013 | Martin | |
| 8,545,526 B2 | 10/2013 | Martin et al. | |
| 8,568,432 B2 | 10/2013 | Straub | |
| 8,574,262 B2 | 11/2013 | Ferrera et al. | |
| 8,579,915 B2 | 11/2013 | French et al. | |

(56) References Cited

U.S. PATENT DOCUMENTS

| | | |
|---|---|---|
| 8,585,713 B2 | 11/2013 | Ferrera et al. |
| 8,696,622 B2 | 4/2014 | Fiorella et al. |
| 8,771,289 B2 | 7/2014 | Mohiuddin et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,345 B2 | 8/2014 | Grandfield et al. |
| 8,801,748 B2 | 8/2014 | Martin |
| 8,814,927 B2 | 8/2014 | Shin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,845,621 B2 | 9/2014 | Fojtik |
| 8,852,205 B2 | 10/2014 | Brady et al. |
| 8,852,226 B2 | 10/2014 | Gilson et al. |
| 8,932,319 B2 | 1/2015 | Martin et al. |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 8,992,504 B2 | 3/2015 | Castella et al. |
| 9,101,382 B2 | 8/2015 | Krolik et al. |
| 9,149,609 B2 | 10/2015 | Ansel et al. |
| 9,161,766 B2 | 10/2015 | Slee et al. |
| 9,204,887 B2 | 12/2015 | Cully et al. |
| 9,259,237 B2 | 2/2016 | Quick et al. |
| 9,283,066 B2 | 3/2016 | Hopkins et al. |
| 9,439,664 B2 | 9/2016 | Sos |
| 9,456,834 B2 | 10/2016 | Folk |
| 9,463,036 B2 | 10/2016 | Brady et al. |
| 9,526,864 B2 | 12/2016 | Quick |
| 9,526,865 B2 | 12/2016 | Quick |
| 9,700,332 B2 | 7/2017 | Marchand et al. |
| 9,717,519 B2 | 8/2017 | Rosenbluth et al. |
| 9,757,137 B2 | 9/2017 | Krolik et al. |
| 2001/0004699 A1 | 6/2001 | Gittings et al. |
| 2001/0041909 A1 | 11/2001 | Tsugita et al. |
| 2002/0022858 A1 | 2/2002 | Demond et al. |
| 2002/0026211 A1 | 2/2002 | Khosravi et al. |
| 2002/0111648 A1 | 8/2002 | Kusleika et al. |
| 2002/0120277 A1 | 8/2002 | Hauschild et al. |
| 2002/0147458 A1 | 10/2002 | Hiblar et al. |
| 2002/0156457 A1 | 10/2002 | Fisher |
| 2003/0100919 A1 | 5/2003 | Hopkins et al. |
| 2003/0114875 A1 | 6/2003 | Sjostrom |
| 2003/0125663 A1 | 7/2003 | Coleman et al. |
| 2003/0135230 A1 | 7/2003 | Massey et al. |
| 2003/0153973 A1 | 8/2003 | Soun et al. |
| 2003/0191516 A1 | 10/2003 | Weldon et al. |
| 2004/0068288 A1 | 4/2004 | Palmer et al. |
| 2004/0073243 A1 | 4/2004 | Sepetka et al. |
| 2004/0133232 A1 | 7/2004 | Rosenbluth et al. |
| 2004/0167567 A1 | 8/2004 | Cano et al. |
| 2004/0199201 A1 | 10/2004 | Kellett et al. |
| 2005/0038468 A1 | 2/2005 | Panetta et al. |
| 2005/0055047 A1 | 3/2005 | Greenhalgh |
| 2005/0119668 A1 | 6/2005 | Teague et al. |
| 2005/0283186 A1 | 12/2005 | Berrada et al. |
| 2006/0020286 A1 | 1/2006 | Niermann |
| 2006/0047286 A1 | 3/2006 | West |
| 2006/0100662 A1 | 5/2006 | Daniel et al. |
| 2006/0224177 A1 | 10/2006 | Finitsis |
| 2006/0229645 A1 | 10/2006 | Bonnette et al. |
| 2006/0253145 A1 | 11/2006 | Lucas |
| 2006/0282111 A1 | 12/2006 | Morsi |
| 2007/0112374 A1 | 5/2007 | Paul, Jr. et al. |
| 2007/0118165 A1 | 5/2007 | DeMello et al. |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0255252 A1 | 11/2007 | Mehta |
| 2007/0288054 A1 | 12/2007 | Tanaka et al. |
| 2008/0015541 A1 | 1/2008 | Rosenbluth et al. |
| 2008/0088055 A1 | 4/2008 | Ross |
| 2008/0167678 A1 | 7/2008 | Morsi |
| 2008/0228209 A1 | 9/2008 | DeMello et al. |
| 2008/0234722 A1 | 9/2008 | Bonnette et al. |
| 2008/0269798 A1 | 10/2008 | Ramzipoor et al. |
| 2009/0018566 A1 | 1/2009 | Escudero et al. |
| 2009/0054918 A1 | 2/2009 | Henson |
| 2009/0062841 A1 | 3/2009 | Amplatz et al. |
| 2009/0069828 A1 | 3/2009 | Martin et al. |
| 2009/0160112 A1 | 6/2009 | Ostrovsky |
| 2009/0163846 A1 | 6/2009 | Aklog et al. |
| 2009/0182362 A1 | 7/2009 | Thompson et al. |
| 2009/0292307 A1 | 11/2009 | Razack |
| 2009/0299393 A1 | 12/2009 | Martin et al. |
| 2010/0087850 A1 | 4/2010 | Razack |
| 2010/0114113 A1 | 5/2010 | Dubrul et al. |
| 2010/0121312 A1 | 5/2010 | Gielenz et al. |
| 2010/0204712 A1 | 8/2010 | Mallaby |
| 2010/0249815 A1 | 9/2010 | Jantzen et al. |
| 2010/0268264 A1 | 10/2010 | Bonnette et al. |
| 2010/0318178 A1 | 12/2010 | Rapaport et al. |
| 2011/0060212 A1 | 3/2011 | Slee et al. |
| 2011/0152993 A1 | 6/2011 | Marchand et al. |
| 2011/0190806 A1 | 8/2011 | Wittens |
| 2011/0196414 A1 | 8/2011 | Porter et al. |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0251629 A1 | 10/2011 | Galdonik et al. |
| 2011/0264133 A1 | 10/2011 | Hanlon et al. |
| 2012/0059309 A1 | 3/2012 | di Palma et al. |
| 2012/0089216 A1 | 4/2012 | Rapaport et al. |
| 2012/0101480 A1 | 4/2012 | Ingle et al. |
| 2012/0101510 A1 | 4/2012 | Lenker et al. |
| 2012/0143239 A1 | 6/2012 | Aklog et al. |
| 2012/0165919 A1 | 6/2012 | Cox et al. |
| 2012/0179181 A1 | 7/2012 | Straub et al. |
| 2012/0197277 A1 | 8/2012 | Stinis |
| 2012/0232655 A1 | 9/2012 | Lorrison et al. |
| 2012/0271231 A1 | 10/2012 | Agrawal |
| 2012/0277788 A1 | 11/2012 | Cattaneo |
| 2013/0066348 A1 | 3/2013 | Fiorella et al. |
| 2013/0144326 A1 | 6/2013 | Brady et al. |
| 2013/0165871 A1 | 6/2013 | Fiorella et al. |
| 2013/0197567 A1 | 8/2013 | Brady et al. |
| 2013/0317589 A1 | 11/2013 | Martin et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0005715 A1 | 1/2014 | Castella et al. |
| 2014/0005717 A1 | 1/2014 | Martin et al. |
| 2014/0025048 A1 | 1/2014 | Ward |
| 2014/0031856 A1 | 1/2014 | Martin |
| 2014/0046243 A1 | 2/2014 | Ray et al. |
| 2014/0121672 A1 | 5/2014 | Folk |
| 2014/0180397 A1 | 6/2014 | Gerberding et al. |
| 2014/0188143 A1 | 7/2014 | Martin et al. |
| 2014/0236219 A1 | 8/2014 | Dubrul et al. |
| 2014/0243882 A1 | 8/2014 | Ma |
| 2014/0318354 A1 | 10/2014 | Thompson et al. |
| 2015/0018860 A1 | 1/2015 | Quick et al. |
| 2015/0018929 A1 | 1/2015 | Martin et al. |
| 2015/0127035 A1 | 5/2015 | Trapp et al. |
| 2015/0150672 A1 | 6/2015 | Ma |
| 2015/0190156 A1 | 7/2015 | Ulm, III |
| 2015/0196380 A1 | 7/2015 | Berrada et al. |
| 2015/0196744 A1 | 7/2015 | Aboytes |
| 2015/0209058 A1 | 7/2015 | Ferrera et al. |
| 2015/0209165 A1 | 7/2015 | Grandfield et al. |
| 2015/0238207 A1 | 8/2015 | Cox et al. |
| 2015/0250578 A1 | 9/2015 | Cook et al. |
| 2015/0265299 A1 | 9/2015 | Cooper et al. |
| 2015/0305756 A1 | 10/2015 | Rosenbluth et al. |
| 2015/0352325 A1 | 12/2015 | Quick |
| 2015/0360001 A1 | 12/2015 | Quick |
| 2015/0374391 A1 | 12/2015 | Quick et al. |

(56) References Cited

U.S. PATENT DOCUMENTS

| | | |
|---|---|---|
| 2016/0008014 A1 | 1/2016 | Rosenbluth et al. |
| 2016/0113666 A1 | 4/2016 | Quick et al. |
| 2016/0143721 A1 | 5/2016 | Rosenbluth et al. |
| 2016/0262790 A1 | 9/2016 | Rosenbluth et al. |
| 2016/0367285 A1 | 12/2016 | Sos |
| 2017/0079672 A1 | 3/2017 | Quick |
| 2017/0105745 A1 | 4/2017 | Rosenbluth et al. |
| 2017/0112513 A1 | 4/2017 | Marchand et al. |
| 2017/0112514 A1 | 4/2017 | Marchand et al. |
| 2017/0189041 A1 | 7/2017 | Cox et al. |
| 2017/0265878 A1 | 9/2017 | Marchand et al. |
| 2017/0325839 A1 | 11/2017 | Rosenbluth et al. |
| 2018/0092652 A1 | 4/2018 | Marchand et al. |

FOREIGN PATENT DOCUMENTS

| | | |
|---|---|---|
| JP | 2004097807 A | 4/2004 |
| JP | 2005230132 A | 9/2005 |
| JP | 2005323702 A | 11/2005 |
| JP | 2006094876 A | 4/2006 |
| JP | 2011526820 | 1/2010 |
| WO | WO-1997017889 A1 | 5/1997 |
| WO | WO-1999044542 | 9/1999 |
| WO | WO-2000053120 | 9/2000 |
| WO | WO-2005046736 | 5/2005 |
| WO | WO-2006110186 | 10/2006 |
| WO | WO-2007092820 A2 | 8/2007 |
| WO | WO-2009155571 A1 | 12/2009 |
| WO | WO2010002549 | 1/2010 |
| WO | WO-2010010545 A1 | 1/2010 |
| WO | WO-2010023671 A2 | 3/2010 |
| WO | WO-2010049121 A2 | 5/2010 |
| WO | WO-2010102307 A1 | 9/2010 |
| WO | WO-2011054531 A2 | 5/2011 |
| WO | WO-2012009675 A2 | 1/2012 |
| WO | WO-2012011097 | 4/2012 |
| WO | WO-2012/065748 A1 | 5/2012 |
| WO | WO-2014047650 A1 | 3/2014 |
| WO | WO-2014081892 A1 | 5/2014 |
| WO | WO-2015006782 A1 | 1/2015 |
| WO | WO-2015061365 A1 | 4/2015 |
| WO | WO2017070702 | 4/2017 |
| WO | WO2018080590 | 5/2018 |

OTHER PUBLICATIONS

English translation of Japanese Office Action received for JP Application No. 2016-564210, Applicant: Inceptus Medical, LLC, dated Sep. 4, 2017, 4 pages.
Australian Exam Report received for AU Application No. 2015274704, Applicant: Inceptus Medical, LLC, dated Sep. 7, 2017, 3 pages.
European Search Report received for EP Application No. 15805810.7, Applicant: Inceptus Medical, LLC, dated Sep. 4, 2017, 6 pages.
European Patent Application No. 13838945.7, Extended European Search Report, 9 pages, dated Apr. 15, 2016.
Final Office Action for U.S. Appl. No. 14/299,933, dated Aug. 12, 2015, 7 pages.
Final Office Action in U.S. Appl. No. 14/299,933, dated Dec. 29, 2014, 15 pages.
Gibbs, et al., "Temporary Stent as a bail-out device during percutaneous transluminal coronary angioplasty: preliminary clinical experience," British Heart Journal, 1994, 71:372-377,Oct. 12, 1993 6 pgs.
Gupta, S. et al., "Acute Pulmonary Embolism Advances in Treatment", JAPI, Association of Physicians India, Mar. 2008, vol. 56, 185-191.
International Search Report and Written Opinion for International App. No. PCT/US13/61470, dated Jan. 17, 2014, 7 pages.
International Search Report and Written Opinion for International App. No. PCT/US2014/046567, dated Nov. 3, 2014, 13 pages.
International Search Report and Written Opinion for International App. No. PCT/US2014/061645, dated Jan. 23, 2015, 15 pages.
International Search Report and Written Opinion for International Application No. PCT/US2015/034987, dated Sep. 17, 2015, 12 pages.
International Search Report for International App. No. PCT/US13/71101, dated Mar. 31, 2014, 4 pages.
Konstantinides, S. et al., "Pulmonary embolism hotline 2012—Recent and expected trials", Thrombosis and Haemostasis, Jan. 9, 2013:33; 43-50.
Konstantinides, S. et al., "Pulmonary embolism: risk assessment and management", European Society of Cardiology; European Heart Journal, Sep. 7, 2012:33, 3014-3022.
Kucher, N. et al., "Percutaneous Catheter Thrombectomy Device for Acute Pulmonary Embolism: In Vitro and In Vivo Testing", Circulation, Sep. 2005:112:e28-e32.
Kucher, N., "Catheter Interventions in Massive Pulmonary Embolism", CardiologyRounds, Mar. 2006 vol. 10, Issue 3, 6 pages.
Kucher, N. et al., "Management of Massive Pulmonary Embolism", Radiology, Sep. 2005:236:3 852-858.
Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.
Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.
Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254.
Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.
Lee, L. et al, "Massive pulmonary embolism: review of management strategies with a focus on catheter-based techniques", Expert Rev. Cardiovasc. Ther. 8(6), 863-873 (2010).
Liu, S. et al, "Massive Pulmonary Embolism: Treatment with the Rotarex Thrombectomy System", Cardiovascular Interventional Radiology; 2011: 34:106-113.
Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.
Non-Final Office Action in U.S. Appl. No. 13/843,742, dated Sep. 13, 2013, 16 pages.
Non-Final Office Action in U.S. Appl. No. 14/299,933, dated Aug. 29, 2014, 10 pages.
Notice of Allowance for U.S. Appl. No. 13/843,742, dated Mar. 12, 2014, 13 pages.
Notice of Allowance for U.S. Appl. No. 14/288,778, dated Dec. 23, 2014, 12 pages.
Reekers, J. et al., "Mechanical Thrombectomy for Early Treatment of Massive Pulmonary Embolism", CardioVascular and Interventional Radiology, 2003: 26:246-250.
Schmitz-Rode et al., "New Mesh Basket for Percutaneous Removal of Wall-Adherent Thrombi in Dialysis Shunts," Cardiovasc Intervent Radiol 16:7-10 1993 4 pgs.
Schmitz-Rode et al., "Temporary Pulmonary Stent Placement as Emergency Treatment of Pulmonary Embolism," Journal of the American College of Cardiology, vol. 48, No. 4, 2006 (5 pgs.).
Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.
Spiotta, A et al., "Evolution of thrombectomy approaches and devices for acute stroke: a technical review." J NeuroIntervent Surg 2015, 7, pp. 7 pages.
Svilaas, T. et al., "Thrombus Aspiration During Primary Percutaneous Coronary Intervention." The New England Journal of Medicine, 2008, vol. 358, No. 6, 11 pages.
Tapson, V., "Acute Pulmonary Embolism", The New England Journal of Medicine, Mar. 6, 2008:358:2037-52.

(56) References Cited

OTHER PUBLICATIONS

The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.
Truong et al., "Mechanical Thrombectomy of Iliocaval Thrombosis Using a Protective Expandable Sheath," Cardiovasc Intervent Radiol27-254-258, 2004, 5 pgs.
Turk et al., "ADAPT FAST study: a direct aspiration first pass technique for acute stroke thrombectomy." J NeuroIntervent Surg, vol. 6, 2014, 6 pages.
Uflacker, R., "Interventional Therapy for Pulmonary Embolism", Journal of Vascular and Interventional Radiology, Feb. 2001: 12:147-164.
Verma, R., MD et al. "Evaluation of a Newly Developed Percutaneous Thrombectomy Basket Device in Sheep With Central Pulmonary Embolisms", *Investigative Raiology*, Oct. 2006, 41, 729-734.
International Search Report and Written Opinion for International App. No. PCT/US2016/067628 filed Dec. 19, 2016, Applicant: Inari Medical, Inc, dated Apr. 10, 2017, 11 pages.
Goldhaber, S. et al. "Percutaneous Mechanical Thrombectomy for Acute Pulmonary Embolism—A Double-Edged Sword," American College of CHEST Physicians, Aug. 2007, 132:2, 363-372.
Goldhaber, S., "Advanced treatment strategies for acute pulmonary embolism, including thrombolysis and embolectomy," Journal of Thrombosis and Haemostasis, 2009: 7 (Suppl. 1): 322-327.
International Search Report and Written Opinion for International App. No. PCT/US2017/029696, Date of Filing: Apr. 26, 2017, Applicant: Inari Medical, Inc, dated Sep. 15, 2017, 19 pages.
International Search Report and Written Opinion for International App. No. PCT/US2016/058536, Date of Filing: Oct. 24, 2016, Applicant: Inari Medical, Inc, dated Mar. 13, 2017, 14 pages.

\* cited by examiner

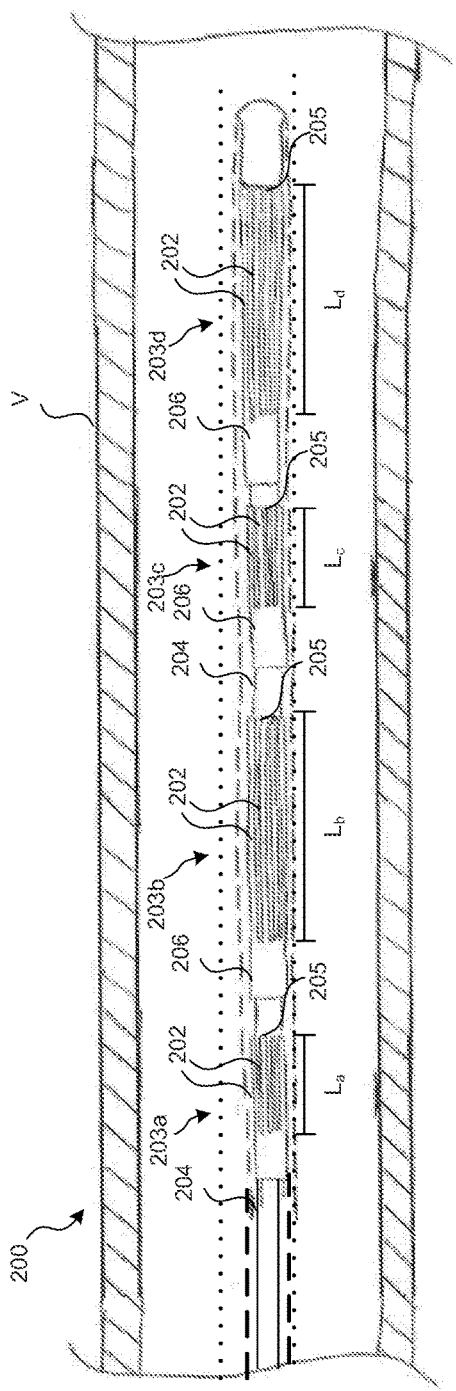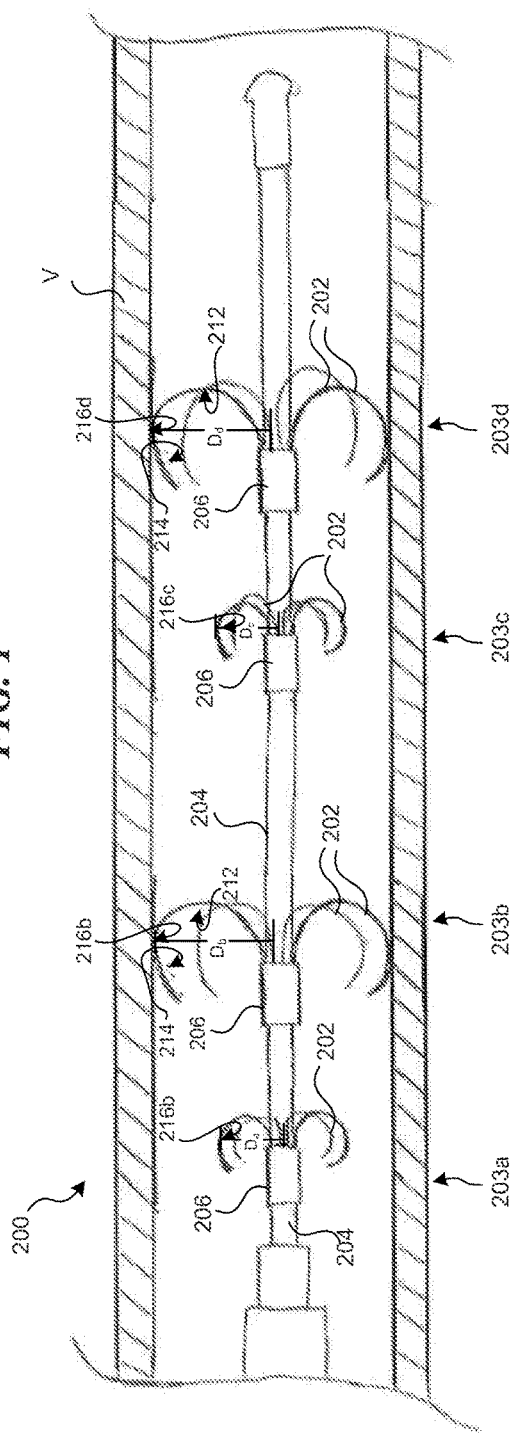

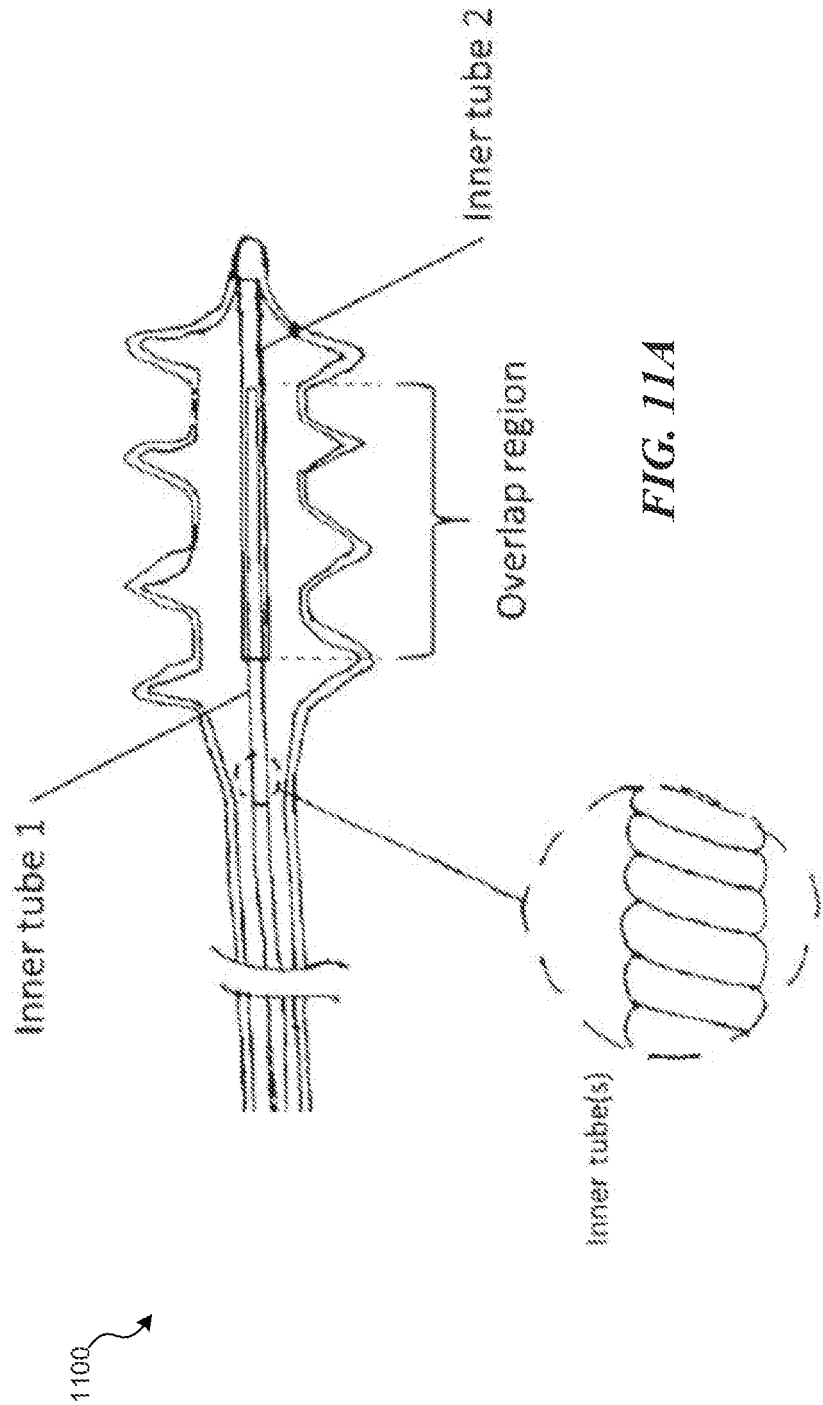

METHODS AND APPARATUS FOR TREATING EMBOLISM

CROSS-REFERENCE TO RELATED APPLICATION(S)

The present application is a 35 U.S.C. 371 of International Application No. PCT/US2014/061645, filed Oct. 21, 2014, entitled "METHODS AND APPARATUS FOR TREATING EMBOLISM," which claims the benefit of the following applications:

(a) U.S. Provisional Patent Application No. 61/893,859, filed Oct. 21, 2013;

(c) U.S. Provisional Patent Application No. 61/949,953, filed Mar. 7, 2014;

(d) U.S. patent application Ser. No. 14/299,933, filed Jun. 9, 2014, now U.S. Pat. No. 9,259,237, issued Feb. 16, 2016; and (e) U.S. patent application Ser. No. 14/299,997, filed Jun. 9, 2014, which has been abandoned.

All of the foregoing applications are incorporated herein by reference in their entireties. Further, components and features of embodiments disclosed in the applications incorporated by reference may be combined with various components and features disclosed and claimed in the present application.

TECHNICAL FIELD

The present technology relates generally to devices and methods for intravascular treatment of emboli within a blood vessel of a human patient.

BACKGROUND

Thromboembolism occurs when a thrombus or blood clot trapped within a blood vessel breaks loose and travels through the blood stream to another location in the circulatory system, resulting in a clot or obstruction at the new location. When a clot forms in the venous circulation, it often travels to the lungs via the heart and lodges within a pulmonary blood vessel PV causing a pulmonary embolism PE. A pulmonary embolism can decrease blood flow through the lungs, which in turn causes decreased oxygenation of the lungs, heart and rest of the body. Moreover, pulmonary embolisms can cause the right ventricle of the heart to pump harder to provide sufficient blood to the pulmonary blood vessels, which can cause right ventricle dysfunction (dilation), and heart failure in more extreme cases.

Conventional approaches to treating thromboembolism and/or pulmonary embolism include clot reduction and/or removal. For example, anticoagulants can be introduced to the affected vessel to prevent additional clots from forming, and thrombolytics can be introduced to the vessel to at least partially disintegrate the clot. However, such agents typically take a prolonged period of time (e.g., hours, days, etc.) before the treatment is effective and in some instances can cause hemorrhaging. Transcatheter clot removal devices also exist, however, such devices are typically highly complex, prone to cause trauma to the vessel, hard to navigate to the pulmonary embolism site, and/or expensive to manufacture. Conventional approaches also include surgical techniques that involve opening the chest cavity and dissecting the pulmonary vessel. Such surgical procedures, however, come with increased cost, procedure time, risk of infection, higher morbidity, higher mortality, and recovery time.

Accordingly, there is a need for devices and methods that address one or more of these deficiencies.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 1 is a side view of one embodiment of a clot treatment device in a low-profile or delivery state positioned in a blood vessel and configured in accordance with the present technology.

FIG. 2 is a side view of the clot treatment device shown in FIG. 1 in an unrestricted expanded or deployed state positioned in a blood vessel and configured in accordance with the present technology.

FIG. 11A is a side cross-sectional view of a clot treatment device configured in accordance with the present technology.

FIG. 11B is an expanded, isolated view of a portion of the clot treatment device shown in FIG. 11A.

DETAILED DESCRIPTION

Figure 3:
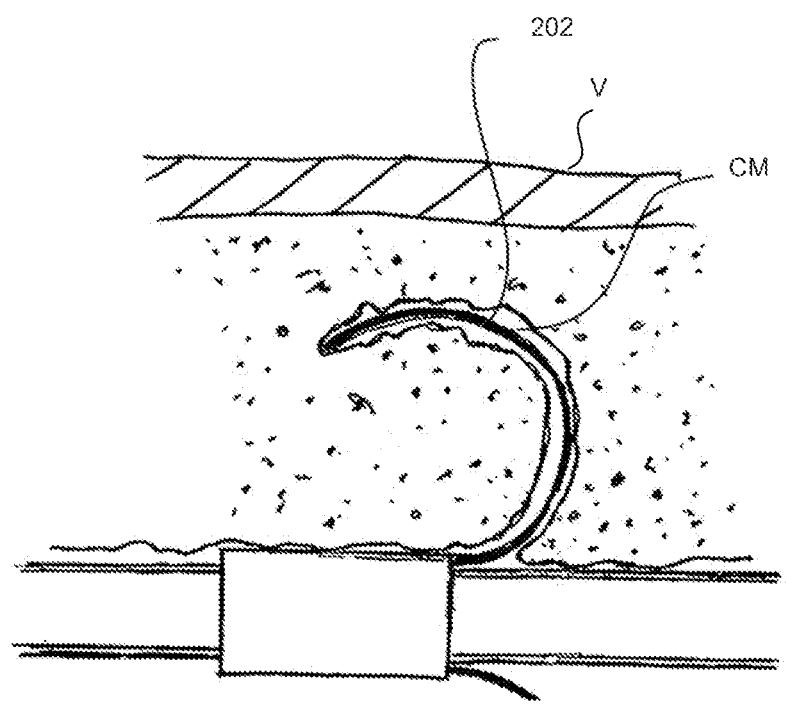
FIG. 3 is a partial side view of the clot treatment device shown in FIG. 2 showing an isolated, deployed clot engagement member within an embolism.

Specific details of several embodiments of clot treatment devices, systems and associated methods in accordance with the present technology are described below with reference to FIGS. 1-14. Although many of the embodiments are described below with respect to devices, systems, and methods for treating an embolism, other applications and other embodiments in addition to those described herein are within the scope of the technology. Additionally, several other embodiments of the technology can have different states, components, or procedures than those described herein. Moreover, it will be appreciated that specific elements, substructures, advantages, uses, and/or other features of the embodiments described with reference to FIGS. 1-14 can be suitably interchanged, substituted or otherwise configured with one another in accordance with additional embodiments of the present technology. Furthermore, suitable elements of the embodiments described with reference to FIGS. 1-14 can be used as standalone and/or self-contained devices. A person of ordinary skill in the art, therefore, will accordingly understand that the technology can have other embodiments with additional elements, or the technology can have other embodiments without several of the features shown and described below with reference to FIGS. 1-14.

With regard to the terms "distal" and "proximal" within this description, unless otherwise specified, the terms can reference a relative position of the portions of a clot treatment device and/or an associated delivery device with reference to an operator and/or a location in the vasculature.

I. SELECTED EMBODIMENTS OF CLOT TREATMENT DEVICES

FIG. 1 is a side view of one embodiment of a clot treatment device 200 ("the device 200") in a low-profile or delivery state positioned in a blood vessel V, and FIG. 2 is a side view of the device 200 in an unrestricted expanded or deployed state that is well suited for removing clot material from a blood vessel (e.g., a pulmonary blood vessel). Referring to FIGS. 1 and 2 together, the device 200 can include a support member 204 and a plurality of treatment portions (referred to collectively as treatment portions 203, referred to individually as first-fourth treatment portions 203a-d, respectively) spaced apart along the support member 204. Each treatment portion 203 can include a hub 206 positioned around the support member 204 and a plurality of clot engagement members 202 integral with and extending distally from the corresponding hub 206 to a distal free end 205. As such, individual treatment portions 203 can include a plurality of clot engagement members 202 positioned about the circumference of the support member 204. Although four treatment portions 203 are shown in FIGS. 1 and 2, in other embodiments the clot treatment device can include more or fewer than four treatment portions 203 (e.g., two treatment portions, three treatment portions, five treatment portions, etc.).

In the delivery state shown in FIG. 1 the clot engagement members 202 can be generally linear and extend generally parallel to the support member 204. The distal ends 205 of the clot engagement members 202 are accordingly the distal-most portion of the clot engagement members 202 in the delivery state. In the expanded state, as shown in FIG. 2, the clot engagement members 202 can project radially outwardly relative to the support member 204 in a curved shape. The clot engagement members 202 can have a proximally facing section 212 which defines a proximally facing concave portion, and, in some embodiments, the clot engagement members 202 can further include an end section 214 that curves radially inwardly from the proximally facing section 212. When deployed within a blood vessel adjacent to clot material, the clot engagement members 202 are configured to penetrate the clot material along an arcuate path and hold clot material to the device 200.

In some embodiments the treatment portions 203 can be fabricated from a single tube (e.g., a hypotube). A plurality of elongated slits may be cut or machined through the wall of the tube by various means known in the art (e.g., conventional machining, laser cutting, electrical discharge machining, photochemical machining, etc.) to form a plurality of clot engagement members 202 that are integral with the corresponding hub 206. In some embodiments, the tube can be cut such that individual clot engagement members 202 can have non-circular cross-sections. The cut tube may then be formed by heat treatment to move from the delivery state shown in FIG. 1 to the deployed state shown in FIG. 2 in which the arcuate clot engagement members 202 project radially outward. As is known in the art of heat setting, a fixture or mold may be used to hold the structure in its desired final configuration and subjected to an appropriate heat treatment such that the clot engagement members 202 assume or are otherwise shape-set to the desire arcuate shape. In some embodiments, the device or component may be held by a fixture and heated to about 475-525° C. for about 5-15 minutes to shape-set the structure. In some embodiments, the treatment portions 203 can be formed from various metals or alloys such as Nitinol, platinum, cobalt-chrome alloys, 35N LT, Elgiloy, stainless steel, tungsten or titanium.

Referring still to FIGS. 1-2, the clot engagement members 202 of different treatment portions 203 can have different lengths (referred to collectively as L, referred to individually as first-fourth lengths $L_a$-$L_b$) in the delivery state (FIG. 1) and thus can extend different distances D from the support member 204 in the deployed state (FIG. 2). As such, deployment of the clot engagement members 202 self-centers the device within the blood vessel V and forces the stiffer, shorter clot engagement members 202 to be positioned radially farther from the vessel wall V. As used herein, "shorter clot engagement members" or "shorter treatment portions" refers to clot engagement members 202 and/or treatment portions 203 with lesser lengths L and/or distances D relative to the other clot engagement members 202 and/or treatment portions 203 of the same clot treatment device, and "longer clot engagement members" or "longer treatment portions" refers to clot engagement members 202 and/or treatment portions 203 with greater lengths L and/or distances D relative to the other clot engagement members 202 and/or treatment portions 203 of the same clot treatment device.

For example, as shown in FIG. 1, in the delivery state, the first treatment portion 203a can have clot engagement members with a first length $L_a$, the second treatment portion 203b can have clot engagement members 202 with a second length $L_b$, the third treatment portion 203c can have clot engagement members 202 with a third length $L_c$, and the fourth treatment portion 203d can have clot engagement members 202 with a fourth length $L_d$. In FIG. 1, the clot engagement member lengths L of adjacent treatment portions 203 alternate between shorter and longer clot engagement members (i.e., clot engagement members 202 of first and third treatment portions 203a, 203c alternate with clot engagement members 202 of the second and fourth treatment portions 203b, 203d along the support member 204). In other words, in the embodiment shown in FIG. 1, the first length $L_a$ is less than the second length $L_b$, the second length $L_b$ is greater than the third length $L_c$, and the third length $L_c$ is less than the fourth length $L_d$. In other embodiments, the clot treatment device 200 and/or treatment portions 203 can have other suitable configurations and/or arrangements. For example, the clot treatment device 200 can include any arrangement of treatment portions 203 having shorter clot engagement members 202 and treatment portions 203 having longer clot engagement members 202 relative to the shorter clot engagement members 202. Moreover, the clot treatment device 200 can have any number of treatment portions 203 having shorter clot engagement members 202 and/or any number of treatment portions 203 having longer clot engagement members 202. Also, clot engagement members 202 having varying lengths need not be in separate treatment portions 203. For example, in some embodiments, one or more treatment portions 203 can include both shorter and longer clot engagement members 202 in the same treatment portion 203.

Referring to FIG. 2, in the deployed state, the clot treatment device 200 can include a first treatment portion 203a having clot engagement members 202 with a radially furthest apex 216a that is a first distance $D_a$ from the support member 204, a second treatment portion 203b having clot engagement members 202 with a radially furthest apex 216b that is a second distance $D_b$ from the support member 204, a third treatment portion 203c having clot engagement members 202 with a radially furthest apex 216c that is a third distance $D_c$ from the support member 204, and a fourth treatment portion 203d having clot engagement members 202 with a radially furthest apex 216d that is a fourth distance $D_d$ from the support member 204. As shown in FIG. 2, the distance D of the radially furthest apex of adjacent treatment portions 203 from the support member 204 can alternate between shorter (clot engagement members 202 of first and third treatment portions 203a, 203c) and longer (clot engagement members 202 of the second and fourth treatment portions 203b, 203d). In other words, in the embodiment shown in FIG. 1, the first distance $D_a$ is less than the second distance $D_b$, the second distance $D_b$ is greater than the third length $D_c$, and the third distance $D_c$ is less than the fourth distance $D_d$. In other embodiments, the clot treatment device 200 and/or treatment portions 203 can have other suitable configurations and/or arrangements. For example, the clot treatment device 200 can include any arrangement of treatment portions 203 having clot engagement members 202 with longer or shorter radially furthest apex distances D. Moreover, the clot treatment device 200 can have any number of treatment portions 203 having shorter clot engagement member radially furthest apex distances D and/or any number of treatment portions 203 having longer clot engagement members radially furthest apex distances D. Also, clot engagement members 202 having varying radially furthest apex distances D need not be in separate treatment portions 203. For example, in some embodiments, one or more treatment portions 203 can include engagement members 202 with both shorter radially furthest apex distances D and longer radially further apex distances D.

Advantageously, clot engagement members 202 having shorter radially furthest apex distances D and/or shorter lengths L can have a greater radial stiffness than clot engagement members 202 having longer radially furthest apex distances D and/or longer lengths L. As shown in the isolated side view of a clot engagement member of FIG. 3, when deployed, the shorter, stiffer clot engagement members 202 can thus be spaced apart from the vessel wall V and grasp a more central portion of the clot material to provide mechanical resilience during withdrawal of the clot material CM while the apices of the longer, more flexible clot engagement members 202 (not shown in FIG. 3) atraumatically engage and slide along the vessel wall V. In some embodiments, the stiffness of the shorter clot engagement members 202 may be from about 150% to about 400% greater than the stiffness of the longer clot engagement members 202. In some embodiments, the type of material, cross-sectional shape and/or area of the individual clot engagement members 202 can also be varied to affect the radial stiffness of the clot engagement members 202. For example, the relatively shorter clot engagement members 202 can be made from a first material and the relatively longer clot engagement members 202 can be made from a second material that is more ductile, elastic, and or flexible than the first material, and/or the shorter clot engagement members 202 can have a great cross-sectional thickness or area than the relatively longer clot engagement members 202.

The clot engagement members 202 can have a single or constant radius of curvature. In other embodiments, the clot engagement members 202 can have a plurality of radii of curvature, such as a first region with a first radius of curvature and a second region with a second radius of curvature. In some embodiments, the clot engagement members 202 can have a single radius of curvature that is the same for all of the clot engagement members 202. In other embodiments, the clot treatment device 200 can have a first group of clot engagement members 202 with a constant radius of curvature and a second group of clot engagement members 202 with a plurality of radii of curvature. Moreover, in additional embodiments the clot treatment device 200 can include a first group of clot engagement members 202 having a first radius of curvature and a second group of clot engagement members 202 having a second radius of curvature different than the first radius of curvature. In some embodiments, the radius of the clot engagement members 202 can be between about 1.5 mm and about 12 mm, and in some embodiments, between about 2 mm and about 12 mm.

Figure 4:
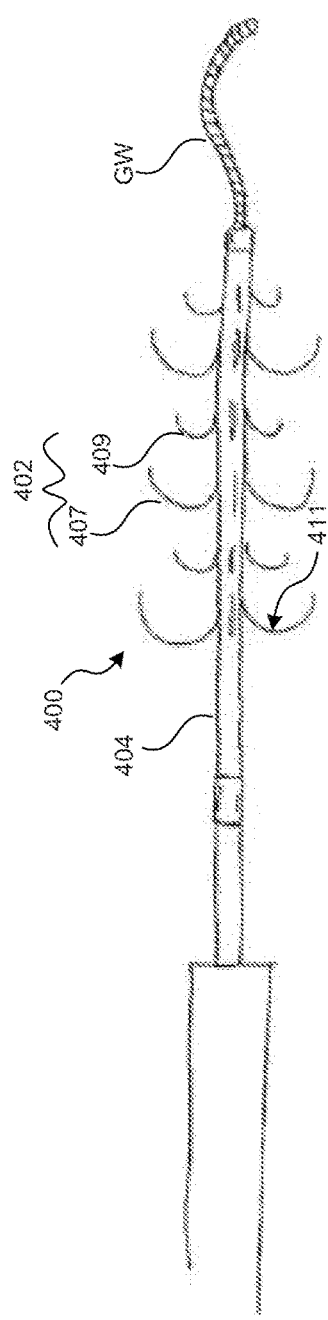
FIG. 4 is a side view of a clot treatment device having distally-facing clot engagement members in a deployed state configured in accordance with another embodiment of the present technology.

FIG. 4 is a side view of another embodiment of a clot treatment device 400 in a deployed state configured in accordance with the present technology. As shown in FIG. 4, the clot treatment device 400 can include a support member 404 and a plurality of clot engagement members 402 positioned about the support member 404. The support member 404 can be an elongated tubular structure that includes a lumen configured to slidably receive a guidewire GW therethrough. As shown in FIG. 4, in the deployed state, the clot engagement members 402 can extend radially outward from the support member 404 and curve distally such that individual clot engagement members 402 include a concave, distally-facing portion 411.

The clot engagement members 402 can be arranged in rows such that adjacent rows along the support member 404 alternate between long 407 and short 409 clot engagement members. Additionally, the short clot engagement members 409 can be circumferentially aligned with the long 407 clot engagement members 407 about the support member 404. In other embodiments, the clot engagement members 402 can have other suitable arrangements and/or configurations. For example, in some embodiments, one or more of the short clot engagement members 409 can be circumferentially offset from one or more of the long clot engagement members 409 about the support member 404, the long and short clot engagement members 407, 409 can be within the same rows, additionally or alternatively arranged in columns, and/or randomly positioned along or about the support member 404.

Figure 5:
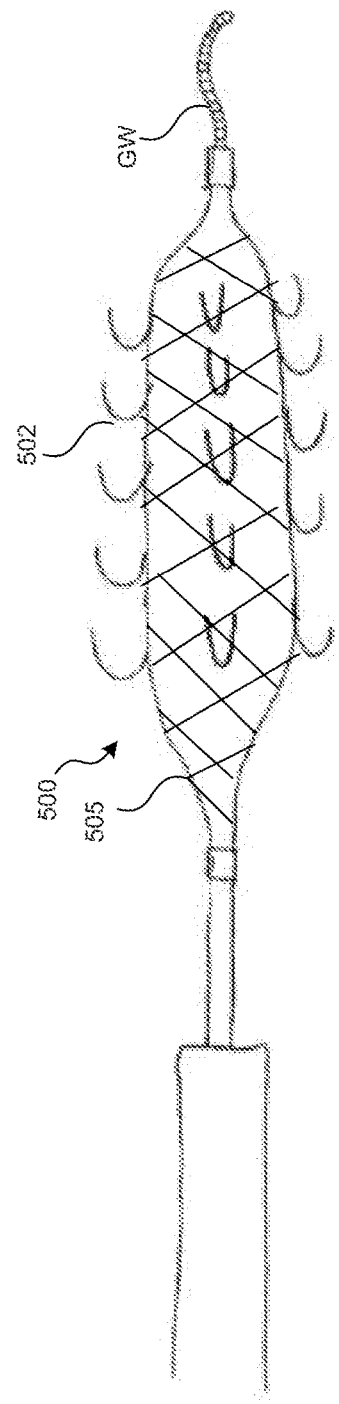
FIG. 5 is a side view of a clot treatment device having distally-facing clot engagement members in a deployed state configured in accordance with another embodiment of the present technology.

FIG. 5 is a side view of another embodiment of a clot treatment device 500 in a deployed state configured in accordance with the present technology. As shown in FIG. 5, the clot treatment device 500 can include an expandable mesh 505 and a plurality of arcuate clot engagement members 502 extending radially outwardly from the expandable mesh 505. Although only distally-facing clot engagement members 502 are shown in FIG. 5, in other embodiments, the clot treatment device 500 can additionally or alternatively include proximally-facing clot engagement members (such as those shown in FIGS. 1-2 and FIG. 3). In some embodiments, the clot engagement members 502 can be interwoven into the mesh structure 505. In other embodiments, the clot engagement members 502 can also be bonded, soldered, welded, tied or otherwise secured and/or mechanically interlocked to the mesh 505.

Figure 6:
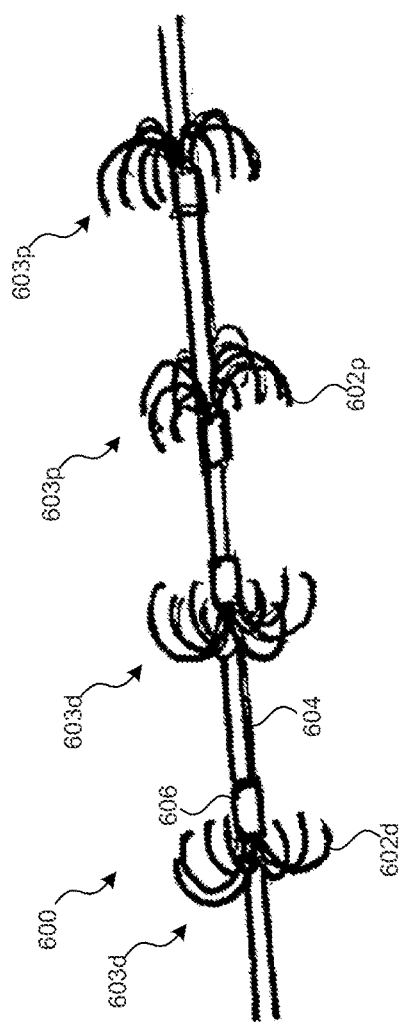
FIG. 6 is a side perspective view of a clot treatment device in a deployed state configured in accordance with another embodiment of the present technology.
Figure 7:
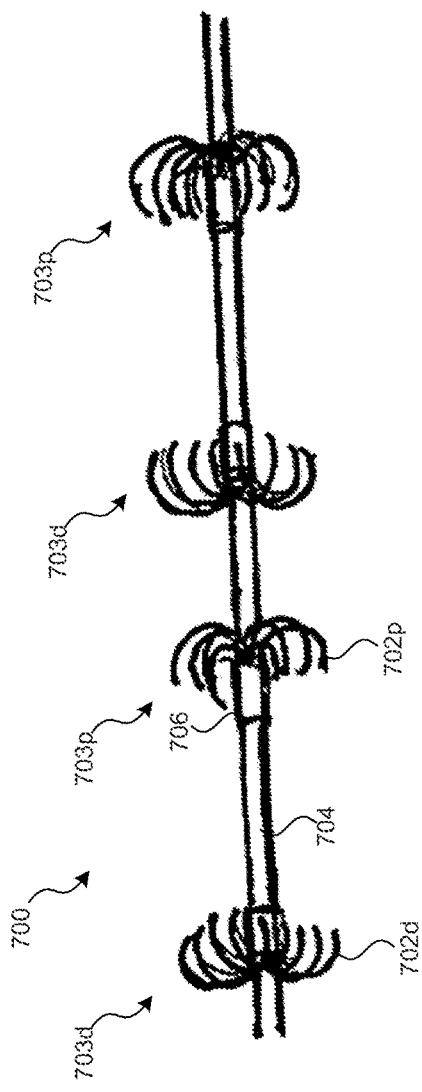
FIG. 7 is a side perspective view of a clot treatment device in a deployed state configured in accordance with another embodiment of the present technology.

In certain procedures, it may be advantageous to move the clot treatment device along the vessel (fully or partially within the embolism) in both the upstream and downstream directions to facilitate engagement and/or disruption of a clot or thrombus by the clot engagement members. During such procedures, it may be advantageous to include one or more distally-facing clot engagement members to enhance engagement and/or disruption of the clot material. Accordingly, the clot treatment devices of the present technology can include both proximally-facing clot engagement members and distally-facing clot engagement members. For example, FIG. 6 is a perspective side view of a portion of a clot treatment device 600 having proximally-facing (e.g., concave proximally) treatment portions 603p (collectively referred to as treatment portions 603) comprised of proximally-facing 602p clot engagement members and distally-facing (e.g., concave distally) treatment portions 603d comprised of distally-facing 602d clot engagement members. As shown in FIG. 6, the distally-facing clot engagement members 602d of the distally-facing treatment portions 603d extend radially outwardly from the corresponding hub 606, then curve distally to a distal free-end. Although the clot treatment device 600 shown in FIG. 6 includes two distally-facing treatment portions 603d and two proximally-facing treatment portions 603p along the support member 604, the clot treatment device 600 can include any arrangement and/or configuration of treatment portions and/or clot engagement members. For example, as shown in the clot treatment device 700 of FIG. 7, the adjacent treatment portions can alternate between those including proximally-facing clot engagement members 702p and distally-facing clot engagement members 703d.

Figure 8:
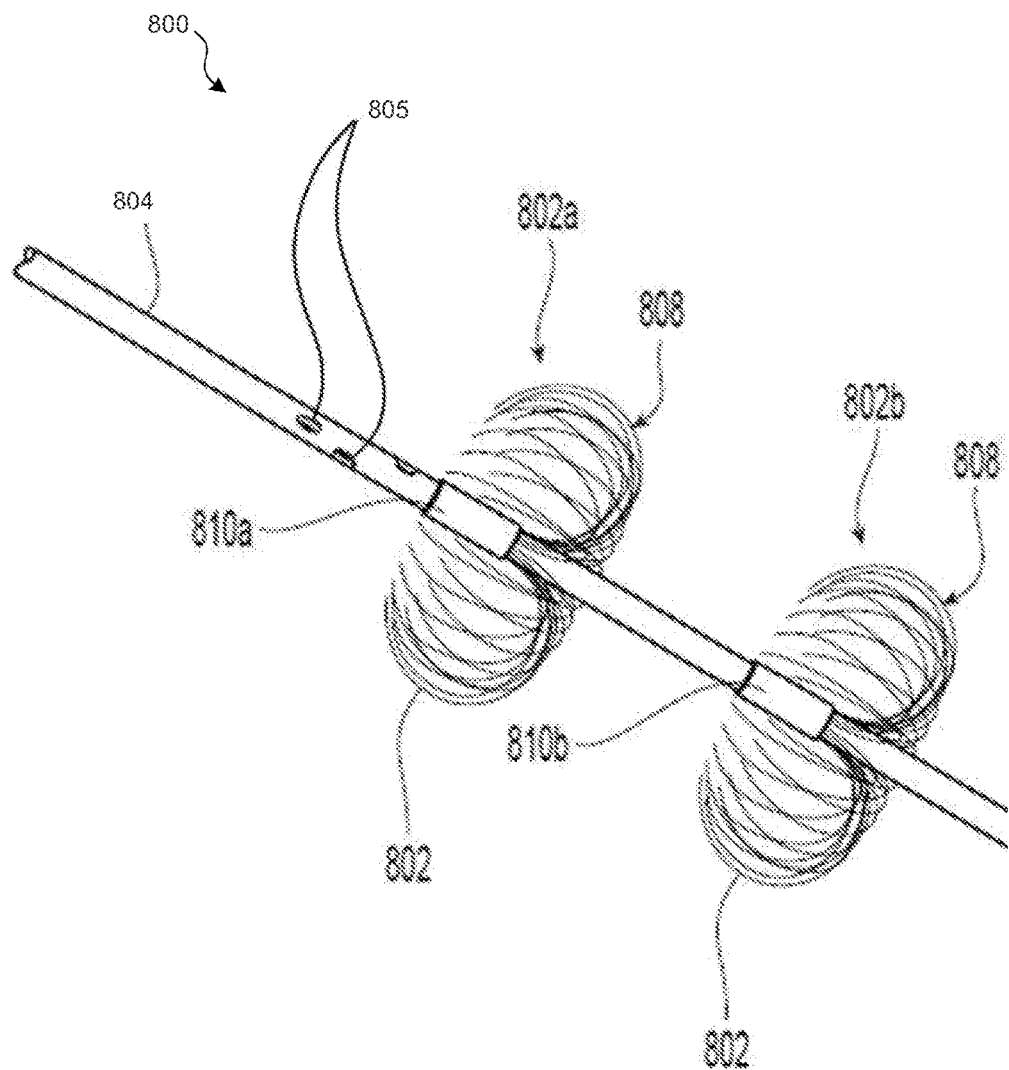
FIG. 8 is a side perspective view of a portion of a clot treatment device in a deployed state having a plurality of ports configured in accordance with another embodiment of the present technology.

FIG. 8 is a side perspective view of a portion of another embodiment of a clot treatment device 800 configured in accordance with the present technology. As shown in FIG. 8, the support member 804 of the clot treatment device 800 can include holes or ports 805 to allow the infusion of fluids (e.g., thrombolytics) along its length and between treatment portions (labeled 802a and 802b). The ports 805 can be positioned anywhere along the length of the support member 804 (e.g., proximal to the proximal-most treatment portion, distal to the distal-most treatment portion, in between treatment portions, etc.). The location of the ports 805 along the length of the support member 804 can enhance the direct infusion of the fluids into the clot and improve the biologic action and effectiveness of such drugs. Additionally, in some embodiments, the clot engagement members can be at least partially hollow and/or include ports or inlets along their lengths and/or at their free-ends.

II. ADDITIONAL EMBODIMENTS OF CLOT TREATMENT DEVICES AND ASSOCIATED DEVICES, SYSTEMS AND METHODS

Figure 9A:
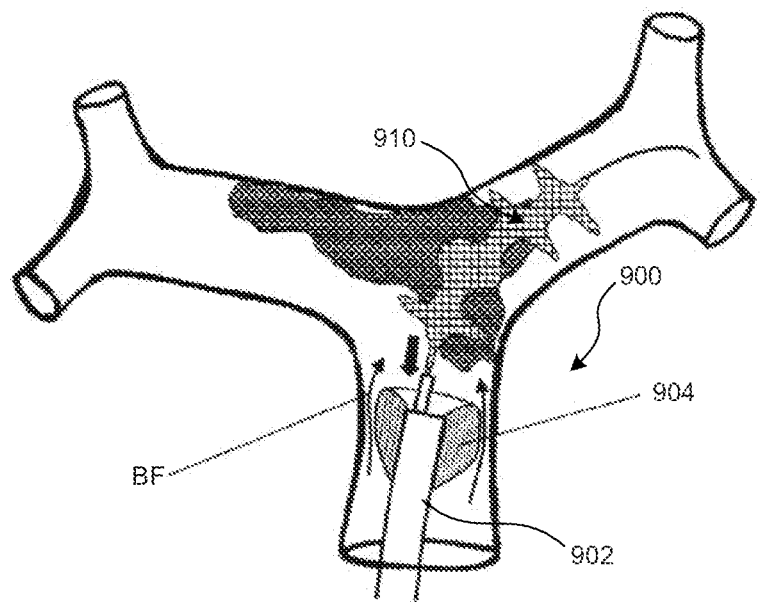
FIG. 9A is a front view of a portion of a delivery system for a clot treatment device that includes an expandable member in a deployed state configured in accordance with an embodiment of the present technology.
Figure 9B:
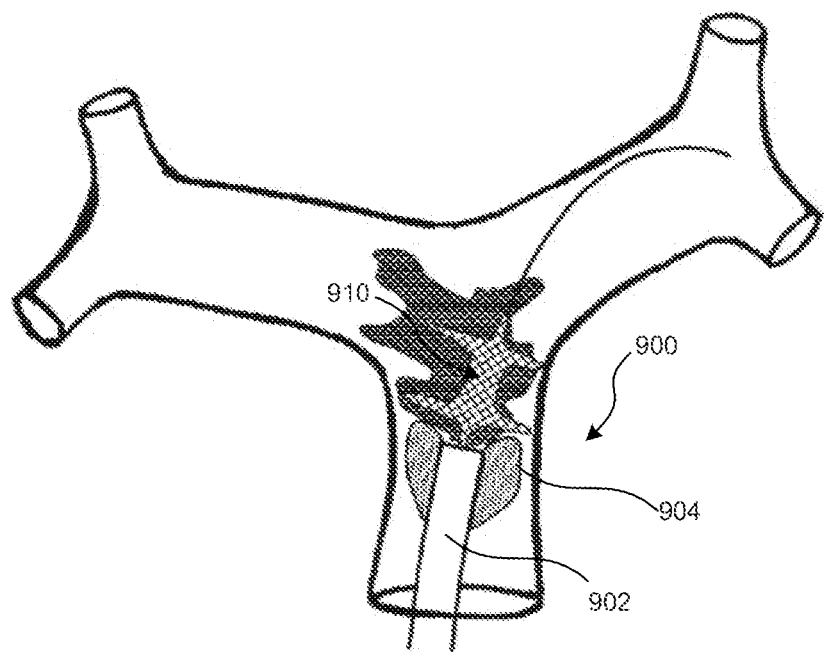
FIG. 9B is a front view of a portion of a delivery system for a clot treatment device that includes an expandable member in a deployed state configured in accordance with another embodiment of the present technology.

FIG. 9 is a front view of a delivery system 900 for use with the clot treatment devices of the present technology. As shown in FIG. 9, the delivery system 900 can include a guide-catheter 902 and an expandable member 904 (e.g., a balloon) coupled to a distal portion of the guide-catheter 902. In such embodiments, the expandable member 904 can be expanded to a diameter less than the vessel diameter, as shown in FIG. 9. Use of the expandable member 904 coupled to the distal portion of the guide catheter 902 can divert flow in the vessel away from the distal portion of the guide catheter 902, thereby reducing or eliminating the possibility of clot material traveling proximal of the device during retraction of the clot treatment device 910 (and adherent clot) into the guide catheter 902 (shown in FIG. 9B). Moreover, the use of an expandable member 904 with the guide catheter 902 can be advantageous as the expandable member 904 can form a funnel adjacent to the distal end of the guide catheter 904, thereby facilitating retraction of the clot material into the guide catheter 904. Additionally, expanding the expandable member 904 to a diameter that is less than the diameter allows some blood flow BF to occur through the vessel near the treatment site, thus reducing any risk associated with complete blockage of blood flow.

Figure 10A:
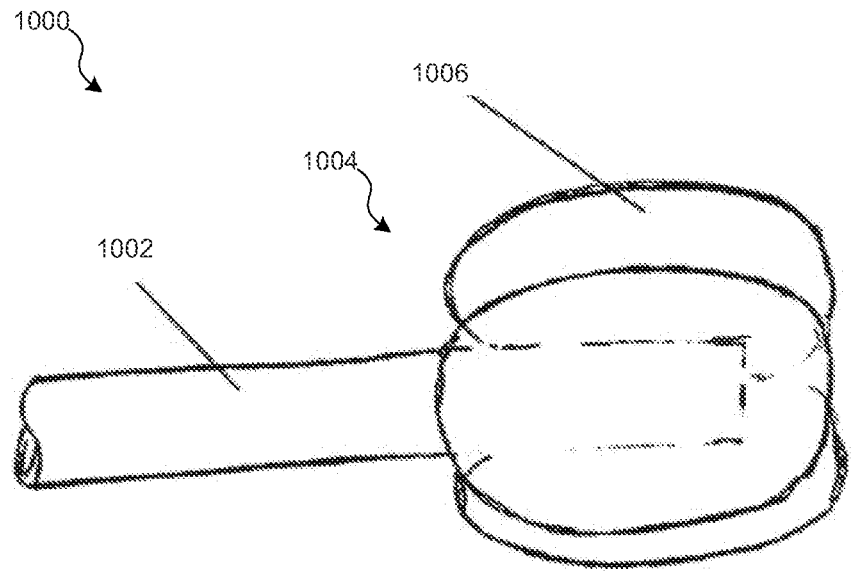
FIG. 10A is a side view of an expandable member configured in accordance with the present technology.
Figure 10B:
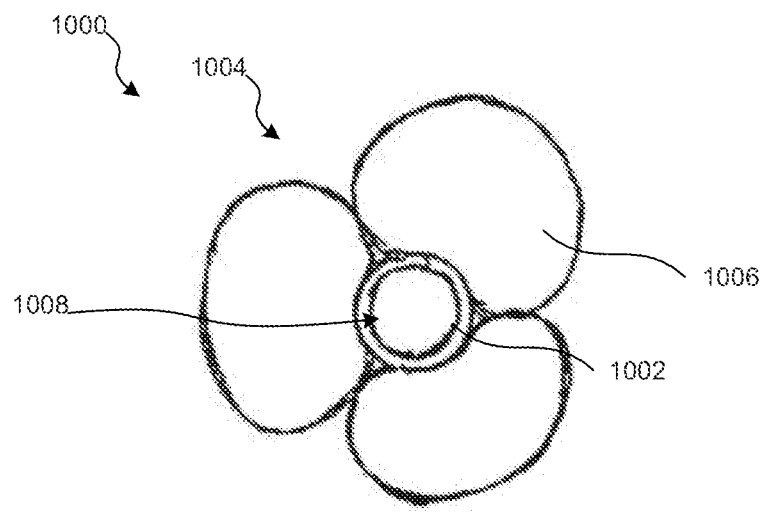
FIG. 10B is an end view of the expandable member shown in FIG. 10A.

FIG. 10A is a side view of a portion of a delivery system 1000 for use with the clot treatment devices of the present technology, and FIG. 10B is a top view of the delivery system shown in FIG. 10A. Referring to FIGS. 10A and 10B together, in those embodiments that include expandable members coupled to a distal portion of the guide catheter, the expandable member can center the guide catheter within the vessel, thereby enhancing and/or facilitating clot removal and/or aspiration. Since the clot treatment device is self-expanding, it will generally tend to self-center within the blood vessel in addition to the centering of the guide catheter enabled by the expandable members of the delivery system. Alignment of the guide catheter and clot treatment device will provide the best situation for guiding of clot to the distal end of the catheter with the least amount of shearing of clot by the distal end of the catheter. Thus, general alignment of the clot treatment device and the guide catheter may improve the efficiency and quality of clot extraction and/or clot aspiration and thereby reduce breakup of the clot and distal embolization. In some embodiments, a multi-lobed expandable member may be used to center the guide catheter within the blood vessel while allowing some blood flow past the expandable members so as to not completely occlude the blood vessel during the procedure. Various multi-lobed expandable member configurations are known in the art including but not limited to a tri-lobed expandable member as shown in FIGS. 10A and 10B.

In any of the clot treatment device embodiments that comprise a central tube member, the inner tube or "tether tube" may be constructed so as to have spring properties. For example, as shown in FIGS. 11A and 11B, the tube may be a coil or spiral cut tube so that when tension is applied, it readily elongates. A spring inner tube member may provide improved self-expansion while still providing a lumen for a guidewire, catheter or the like to be inserted therethrough. Moreover, the inner tube or "tether tube" may be constructed with a first proximal tube that is attached to the clot treatment device proximal to the radially expanding segment and a second distal tube that is attached to the clot treatment device distal to the radially expanding segment. One tube may be larger in diameter than the other so that they may be over-lapped with a portion where the smaller tube is coaxial within the larger tube and thus "telescoped" as shown in FIGS. 11A and 11B. In this telescoped configuration, the tubes may slide freely relative to each other. Thus, with a telescoped inner tube configuration, a guidewire lumen is maintained while allowing a large elongation without plastic deformation.

Figure 12:
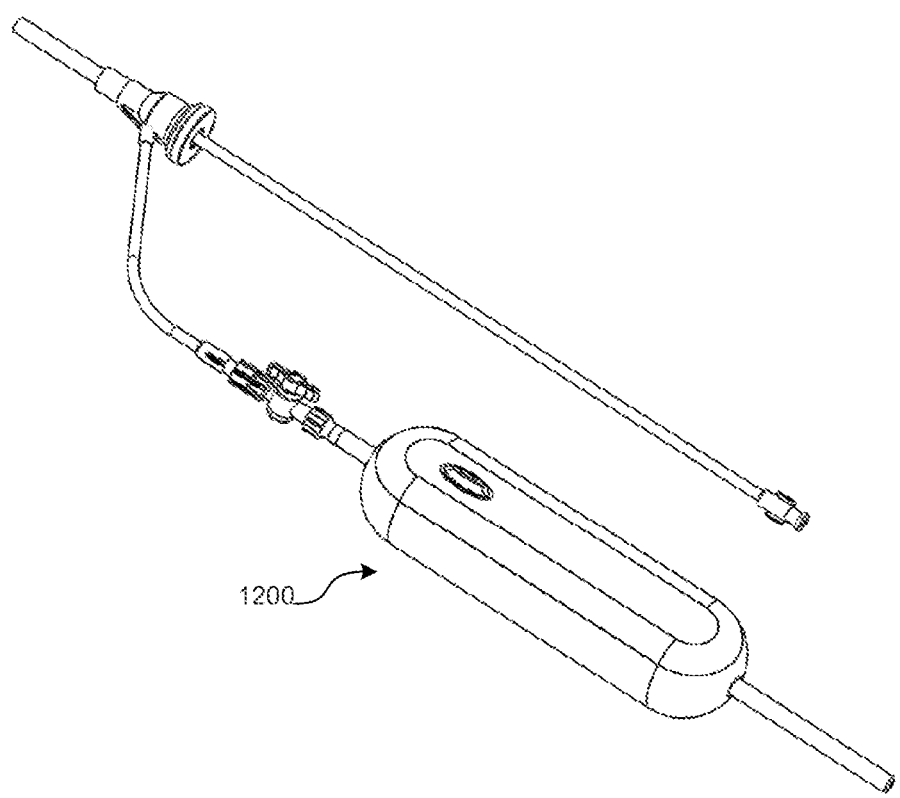
FIG. 12 is a pressure-generating member configured in accordance with the present technology.
Figure 14:
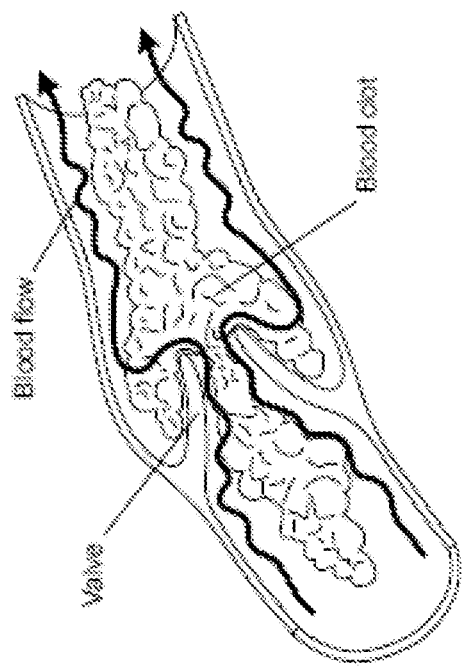
FIG. 14 is an enlarged schematic representation of a deep vein thrombosis.
Figure 13:
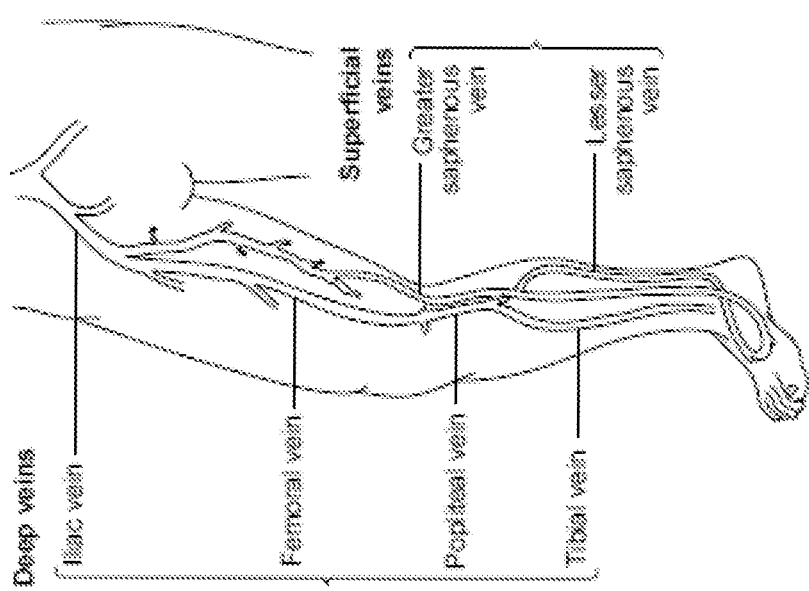
FIG. 13 is a schematic representation of the venous system of a human leg.

Now referring to FIG. 12, in some embodiments, parts of the system that retract and/or aspirate fluid and debris may be automated. For example, the movement of the pump (e.g. syringe) plunger may have a mechanism such as a linear actuator, drive screw or the like to effect movement under electronic control. Likewise, the linear movement of the device and delivery catheter for deployment and/or retraction may also be operated by a mechanism. In some embodiments, both the pump and the catheter and device movements may be mechanized and synchronized. In addition, sensors may be incorporated into the system on either the device and/or catheters such that the system will automatically turn mechanisms on/off as desired. This automation may be further controlled by a programmable controller, computer or electronics and software as is well-known in the art of automation. In some embodiments, the system may automatically shut off aspiration when a predetermined amount of device retraction has taken place. That way, the amount of blood that is aspirated is limited. In some embodiments, a continuously aspirating pump mechanism rather than the discrete pump (e.g. syringe) as described herein may be used. The use of a foot petal, a hand switch or an automated or sensor actuated control to limit the duration of a continuous pump may allow smooth continuous aspiration during device retraction without excessive blood being removed from the patient. This may be accomplished by having the pump operate for a relatively short duration or pulses. In some embodiments, the pump may operate for less than about 15 seconds and in other embodiments less that about 5 seconds. A diagram of such a system with a continuous aspiration pump is shown in Figure F. In some embodiments, a method of synchronized device retraction and aspiration is described wherein less than about 500 cc of blood and debris are removed from the patient. In other embodiments, the device may be retracted with aspiration of between about 50 cc and 400 cc, in some embodiments less than about 200 cc and in some embodiments less than about 100 cc of blood and debris.

III. PERTINENT ANATOMY AND PHYSIOLOGY

Some embodiments described here may be particularly useful for the treatment of deep vein thrombosis. (See FIGS. 13 and 14). Deep vein thrombosis (DVT) is a medical condition that results from the formation of a blood clot, or thrombus, within a vein. Thrombi may develop in the veins of the calves, legs, arms, pelvis or abdomen, but they may occur in other locations as well. The clot is typically formed from a pooling of blood within the vein due to abnormally long periods of rest or inactivity, e.g. when an individual is bed ridden following surgery or suffering a debilitating illness or during extended airline flights. The propensity to form clots can be also be influenced by other factors including, coagulation disorders, the presence of cancer, dehydration, hormone replacement therapy, use of birth control pills, genetic deficiencies, autoimmune disorders, and endothelial cell injury and trauma, etc. Thrombi are likely to form at the location of a stenosis (e.g., an unnatural narrowing of an artery). Clots often form near the venous valves; one-way valves that prevent the back-flow of blood as it returns to the right heart (blood is squeezed up the leg against gravity and the valves prevent it from flowing back to our feet). Clinical sequelae of DVT are significant in both the acute and chronic settings. Initial consequences include acute lower-extremity symptoms, risk of pulmonary emboli (PE) and death. Long-term consequences include recurrent DVT, lower-extremity venous hypertension, claudication, pain, swelling and ulceration, which can result in significant post-thrombotic morbidity. Potentially thromboembolic DVT usually arises in one of the large deep veins of the lower limb (e.g. iliac and femoral veins). Patients with iliofemoral DVT tend to have marked pain and swelling and up to 50% experience pulmonary embolism.

Percutaneous access for endovascular interventions is most often achieved in the vein distal to the occluded segment. For isolated iliac DVT, an ipsilateral common femoral puncture is most appropriate. Alternatively, a retrograde approach from either the jugular, iliac vein or the contralateral femoral vein may be used for isolated iliac and femoral vein DVT. More commonly, however, patients present with more extensive iliofemoral or iliofemoral popliteal thrombosis, in which case access is best obtained from the ipsilateral popliteal vein while the patient is positioned prone. Ultrasound guidance may be used for access of the popliteal or tibial veins and for any access obtained while the patient is fully anticoagulated. Further, a micropucture technique with a 22-gauge needle and 0.014-inch guidewire may minimize bleeding complications and vessel wall trauma. Following initial access, the thrombus is crossed with a guidewire to facilitate catheter or device positioning. For a lower puncture location (i.e., closer to the feet) such as the popliteal, a suitable (e.g., less than 10 F) catheter introducer sheath (such as a Flexor® manufactured by Cook, Inc. of Bloomington, Ind.) may be introduced into the vein over a guidewire. If alternate access is done for a retrograde approach to the thrombosis, a larger introducer (up to about 22 F) may be used. If a downstream access is made and then a retrograde approach to the thrombus is done, an expandable tip catheter such as that shown in FIGS. 20 and 21 (PCT/US13/61470) may help prevent clot or debris that may be dislodged or embolized during the procedure from traveling toward the heart. Alternatively, if a lower or upstream access to the vein and then antegrade approach to the thrombus is made, an occlusion device such as a balloon or a filtration/capture device such a distal protection device may be place downstream of the thrombus. For example, a distal protection device may inserted into the iliac or IVC for a contralateral vein. An exemplary distal protection device is the SpiderFX™ Embolic Protection Device commercially available from Covidien (Plymouth, Minn.).

IV. EXAMPLES

The following examples are illustrative of several embodiments of the present technology:

1. A clot treatment device for treating an embolism within a blood vessel, the clot treatment device comprising:
   a support member configured to extend through a delivery catheter, wherein the support member has a proximal portion and a distal portion;
   a plurality of first clot engagement members positioned about the circumference of the distal portion of the support member, wherein, in the deployed state, individual first clot engagement members extend radially outwardly with respect to the support member and have a curved portion that includes a first radially furthest apex that extends a first radial distance from the support member;

a plurality of second clot engagement members positioned about the circumference of the distal portion of the support member, wherein, in the deployed state, individual second clot engagement members have a curved portion that includes a second radially furthest apex that extends a second radial distance from the support member, and wherein the first radial distance is greater than the second radial distance;

wherein, in the deployed state, individual curved portions of the first and second clot engagement members project radially outwardly relative to the support member in a curve that has a proximally extending section which defines a proximally facing concave portion, and wherein the curved portion of the first and second clot engagement members further includes an end section that curves radially inwardly from the proximally extending section; and wherein the clot engagement members are configured to penetrate clot material along an arcuate path and hold clot material to the clot treatment device.

2. The clot treatment device of example 1, further comprising:

a first hub positioned around the support member at a first location; and a second hub positioned around the support member at a second location spaced apart from the first location along the support member;

wherein— individual first clot engagement members extend from the first hub, wherein a proximal portion of the first clot engagement members are integral with the first hub; and individual second clot engagement members extend from the second hub, wherein a proximal portion of the second clot engagement members are integral with the second hub.

3. The clot treatment device of any of examples 1 or 2 wherein:

at least one of the first radially furthest apices of the individual first clot engagement members are configured to engage the vessel wall in a deployed state; and none of the second radially furthest apices of the individual first clot engagement members are configured to engage the vessel wall in a deployed state.

4. The clot treatment device of any of examples 1-3 wherein the first clot engagement members have a first stiffness and the second clot engagement members have a second stiffness greater than the first stiffness.

5. The clot treatment device of any of examples 1-4 wherein:

the first clot engagement members are positioned about the support member at a first location along the length of the support member; and the second clot engagement members are positioned about the support member at a second location along the length of the support member that is spaced longitudinally apart from the first location along the support member.

6. The clot treatment device of any of examples 1-5, further comprising:

a plurality of third clot engagement members positioned about the circumference of the distal portion of the support member, wherein, in the deployed state, individual third clot engagement members extend radially outwardly with respect to the support member and have a curved portion that includes a third radially furthest apex that extends a third radial distance from the support member; and wherein the third radial distance is substantially the same as the first radial distance.

7. The clot treatment device of example 6, further comprising:

a plurality of fourth clot engagement members positioned about the circumference of the distal portion of the support member, wherein, in the deployed state, individual fourth clot engagement members extend radially outwardly with respect to the support member and have a curved portion that includes a fourth radially furthest apex that extends a fourth radial distance from the support member; and wherein the fourth radial distance is substantially the same as the second radial distance.

8. The clot treatment device of example 7 wherein:

the first clot engagement members are positioned at a first location along the length of the support member;

the second clot engagement members are positioned at a second location along the length of the support member that is different than the first location;

the third clot engagement members are positioned at a third location along the length of the support member that is different than the first and second locations;

the fourth clot engagement members are positioned at a fourth location along the length of the support member that is different than the first, second, and third locations.

9. The clot treatment device of any of examples 1-5 and 7, further comprising:

a plurality of third clot engagement members positioned about the circumference of the distal portion of the support member, wherein, in the deployed state, individual third clot engagement members extend radially outwardly with respect to the support member and have a curved portion that includes a third radially furthest apex that extends a third radial distance from the support member; and wherein the third radial distance is different than the second radial distance and the first radial distance.

10. The clot treatment device of any of examples 1-5 and 7, further comprising:

a plurality of third clot engagement members positioned about the circumference of the distal portion of the support member, wherein, in the deployed state, individual third clot engagement members extend radially outwardly with respect to the support member and have a curved portion that includes a third radially furthest apex that extends a third radial distance from the support member; and wherein, in the deployed state, individual curved portions of the third engagement members project radially outwardly relative to the support member in a curve that has a distally extending section which defines a distally facing concave portion, and wherein the curved portion of individual third engagement members further includes an end section that curves radially inwardly from the distally extending section.

11. A treatment device for treating an embolism within a blood vessel, the clot treatment device moveable between a low-profile undeployed state and a deployed state, the clot treatment device comprising:

a support member configured to extend through a delivery catheter, wherein the support member has a proximal portion and a distal portion;

a plurality of first clot engagement members positioned about the circumference of the distal portion of the support member, wherein, in the undeployed state, individual first clot engagement members are linear and have a first length;

a plurality of second clot engagement members positioned about the circumference of the distal portion of the support member, wherein, in the undeployed state, individual second clot engagement members are linear and have a second length that is less than the first length;

wherein, in the deployed state, the individual first and second clot engagement members project radially outwardly relative to the support member in a curve that has a proximally extending section which defines a proximally facing concave portion, and wherein the clot engagement members are configured to penetrate clot material along an arcuate path and hold clot material to the clot treatment device.

12. The clot treatment device of example 11 wherein the curved portion further includes an end section that curves radially inwardly from the proximally extending section.

13. The clot treatment device of any of examples 11-12 wherein, in the undeployed state:

individual first clot engagement members are positioned parallel to the support member; and individual second clot engagement members positioned parallel to the support member.

14. The clot treatment device of any of examples 11-13, further comprising:

a first hub positioned around the support member at a first location; and a second hub positioned around the support member at a second location spaced apart from the first location along the support member;

wherein— individual first clot engagement members extend distally from the first hub in the undeployed state, wherein a proximal portion of the first clot engagement members are integral with the first hub; and individual second clot engagement members extend distally from the second hub in the undeployed state, wherein a proximal portion of the second clot engagement members are integral with the second hub.

VI. CONCLUSION

The above detailed descriptions of embodiments of the present technology are for purposes of illustration only and are not intended to be exhaustive or to limit the present technology to the precise form(s) disclosed above. Various equivalent modifications are possible within the scope of the present technology, as those skilled in the relevant art will recognize. For example, while steps may be presented in a given order, alternative embodiments may perform steps in a different order. The various embodiments described herein and elements thereof may also be combined to provide further embodiments. In some cases, well-known structures and functions have not been shown or described in detail to avoid unnecessarily obscuring the description of embodiments of the present technology.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A clot treatment device for treating an embolism within a blood vessel, the clot treatment device comprising:

a support member configured to extend through a delivery catheter, wherein the support member has a proximal portion and a distal portion;

a plurality of first clot engagement members positioned about the circumference of the distal portion of the support member, wherein, in deployed state, individual first clot engagement members extend radially outwardly with respect to the support member and have a curved portion that includes a first radially furthest apex that extends a first radial distance from the support member;

a plurality of second clot engagement members positioned about the circumference of the distal portion of the support member, wherein, in the deployed state, individual second clot engagement members have a curved portion that includes a second radially furthest apex that extends a second radial distance from the support member, and wherein the first radial distance is greater than the second radial distance;

wherein, in the deployed state, individual curved portions of the first and second clot engagement members project radially outwardly relative to the support member in a curve that has a proximally extending section which defines a proximally facing concave portion, and wherein the curved portion of the first and second clot engagement members further includes an end section that curves radially inwardly from the proximally extending section;

wherein the first clot engagement members have a first stiffness and the second clot engagement members have a second stiffness greater than the first stiffness, and wherein the clot engagement members are configured to penetrate clot material along an arcuate path and hold clot material to the clot treatment device.

2. The clot treatment device of claim 1, further comprising:
a first hub positioned around the support member at a first location; and
a second hub positioned around the support member at a second location spaced apart from the first location along the support member;
wherein—
individual first clot engagement members extend from the first hub, wherein a proximal portion of the first clot engagement members are integral with the first hub; and
individual second clot engagement members extend from the second hub, wherein a proximal portion of the second clot engagement members are integral with the second hub.

3. The clot treatment device of claim 1 wherein:
at least one of the first radially furthest apices of the individual first clot engagement members are configured to engage the vessel wall in the deployed state; and
none of the second radially furthest apices of the individual second clot engagement members are configured to engage the vessel wall in the deployed state.

4. The clot treatment device of claim 1 wherein:
the first clot engagement members are positioned about the support member at a first location along the length of the support member; and
the second clot engagement members are positioned about the support member at a second location along the length of the support member that is spaced longitudinally apart from the first location along the support member.

5. The clot treatment device of claim 1, further comprising:
a plurality of third clot engagement members positioned about the circumference of the distal portion of the support member, wherein, in the deployed state, individual third clot engagement members extend radially outwardly with respect to the support member and have a curved portion that includes a third radially furthest apex that extends a third radial distance from the support member; and
wherein the third radial distance is substantially the same as the first radial distance.

6. The clot treatment device of claim 5, further comprising:
a plurality of fourth clot engagement members positioned about the circumference of the distal portion of the support member, wherein, in the deployed state, individual fourth clot engagement members extend radially outwardly with respect to the support member and have a curved portion that includes a fourth radially furthest apex that extends a fourth radial distance from the support member; and wherein the fourth radial distance is substantially the same as the second radial distance.

7. The clot treatment device of claim 6 wherein:
the first clot engagement members are positioned at a first location along the length of the support member;
the second clot engagement members are positioned at a second location along the length of the support member that is different than the first location;
the third clot engagement members are positioned at a third location along the length of the support member that is different than the first and second locations;
the fourth clot engagement members are positioned at a fourth location along the length of the support member that is different than the first, second, and third locations.

8. The clot treatment device of claim 1, further comprising:
a plurality of third clot engagement members positioned about the circumference of the distal portion of the support member, wherein, in the deployed state, individual third clot engagement members extend radially outwardly with respect to the support member and have a curved portion that includes a third radially furthest apex that extends a third radial distance from the support member; and
wherein the third radial distance is different than the second radial distance and the first radial distance.

9. The clot treatment device of claim 1, further comprising:
a plurality of third clot engagement members positioned about the circumference of the distal portion of the support member, wherein, in the deployed state, individual third clot engagement members extend radially outwardly with respect to the support member and have a curved portion that includes a third radially furthest apex that extends a third radial distance from the support member; and
wherein, in the deployed state, individual curved portions of the third engagement members project radially outwardly relative to the support member in a curve that has a distally extending section which defines a distally facing concave portion, and wherein the curved portion of individual third engagement members further includes an end section that curves radially inwardly from the distally extending section.

10. A clot treatment device for treating an embolism within a blood vessel, the clot treatment device moveable between a low-profile undeployed state and a deployed state, the clot treatment device comprising:
a support member configured to extend through a delivery catheter, wherein the support member has a proximal portion and a distal portion;
a plurality of first clot engagement members positioned about the circumference of the distal portion of the support member, wherein, in the undeployed state, individual first clot engagement members are linear and have a first length;
a plurality of second clot engagement members positioned about the circumference of the distal portion of the support member, wherein, in the undeployed state, individual second clot engagement members are linear and have a second length that is less than the first length;
wherein, in the deployed state, the individual first and second clot engagement members project radially outwardly relative to the support member in a curve that has a proximally extending section which defines a proximally facing concave portion, and wherein the clot engagement members are configured to penetrate clot material along an arcuate path and hold clot material to the clot treatment device.

11. The clot treatment device of claim 10 wherein the curve further includes an end section that curves radially inwardly from the proximally extending section.

12. The clot treatment device of claim 10 wherein, in the undeployed state:

individual first clot engagement members are positioned parallel to the support member; and individual second clot engagement members are positioned parallel to the support member.

13. The clot treatment device of claim 10, further comprising:

a first hub positioned around the support member at a first location; and a second hub positioned around the support member at a second location spaced apart from the first location along the support member;

wherein— individual first clot engagement members extend distally from the first hub in the undeployed state, wherein a proximal portion of the first clot engagement members are integral with the first hub; and individual second clot engagement members extend distally from the second hub in the undeployed state, wherein a proximal portion of the second clot engagement members are integral with the second hub.

* * * * *